United States Patent [19]
Hewitt et al.

[11] Patent Number: 5,893,642
[45] Date of Patent: Apr. 13, 1999

[54] MIXER AND APPARATUS FOR ANALYZING FLUID FLOW

[75] Inventors: Geoffrey Frederick Hewitt, Wallingford; George Lister Shires, Dorset; Susan Joan Parry, Woking; Philip Antony Mark, Chester; Paul Stephen Harrison, Salop, all of United Kingdom

[73] Assignees: I.C. Consultants Limited, London; SGS Redwood Limited, South Wirral, both of United Kingdom

[21] Appl. No.: 08/809,642

[22] PCT Filed: Sep. 27, 1995

[86] PCT No.: PCT/GB95/02294

§ 371 Date: Aug. 29, 1997

§ 102(e) Date: Aug. 29, 1997

[87] PCT Pub. No.: WO96/09880

PCT Pub. Date: Apr. 4, 1996

[30] Foreign Application Priority Data

Sep. 28, 1994 [GB] United Kingdom ............... 9419520

[51] Int. Cl.$^6$ ................ B01F 5/00; G01N 21/85
[52] U.S. Cl. ................ 366/338; 366/142; 73/61.48
[58] Field of Search ................ 366/338, 337, 366/339, 336, 142; 138/42; 73/53.01, 54.39, 54.43, 61.41, 61.43, 61.44, 61.46, 61.47, 61.48, 61.52

[56] References Cited

U.S. PATENT DOCUMENTS 4,318,623   3/1982   Curtis ................ 366/336

*Primary Examiner*—Tony G. Soohoo
*Attorney, Agent, or Firm*—Marshall & Melhorn

[57] ABSTRACT

A static mixer is provided for one or more fluids flowing in a pipe, such as oil, water and gas from an oil well. The mixer comprises an element to divide the flowing fluids into at least two streams within the pipe and to deflect two of the resulting streams so that those streams rotate in opposite senses about axes parallel to the direction of flow of the fluid, the element being shaped so as to maintain movement of the flow in a substantially smooth manner. The apparatus is provided for analyzing fluid flow in a pipe comprising at least one radiation source to direct radiation through the flow, and at least one radiation detector positioned to receive from the source of radiation which has pass through the flow. The source or sources emits radiation at least at two different energies. The detector provides a signal to a processing unit which is arranged to process the signal to provide a series of chronological values, to group the values by magnitude and to analyze the grouped values to determine phase fraction, type of flow e.g. slug flow and flow rate.

16 Claims, 4 Drawing Sheets

MIXER AND APPARATUS FOR ANALYZING FLUID FLOW

The invention relates to a mixer and apparatus for analysing fluid flow.

Mixers are widely used in a number of industries. One such industry is the oil industry. Oil wells produce a mixture of oil, water and gas and homogenisation of these components is desirable for accurate flow measurement.

EP 0395635 discloses a number of static mixer devices. One such device has a plate arranged normal to the flow through the pipe. The plate has two apertures and two curved vanes of sheet material lie directly behind these apertures. Fluids flowing in the pipe will pass through one or other of the apertures to be divided into two streams and will be deflected by the vanes to rotate in opposite senses about axes parallel to the direction of flow of the fluid and will thus be homogenised.

According to one aspect of the present invention there is provided a static mixer for one or more fluids flowing in a pipe, the mixer comprising an element to divide the flowing fluids into at least two streams within the pipe and to deflect two of the resulting streams so that those streams rotate in opposite senses about axes parallel to the direction of flow of the fluid, the element being shaped so as to maintain movement of the flow in a substantially smooth manner.

In this way, effective homogenisation can be obtained without introducing unnecessary turbulence or otherwise unduly disturbing the flow.

The mixer of the invention provides adequate mixing over a wide range of flow conditions thus allowing accurate measurements to be made of phase fraction and velocity at points downstream of the mixer using single narrow gamma or X-ray beams or other established techniques.

Without adequate mixing the phases are not homogeneously distributed across the pipe section, with the result that a single narrow beam may give an erroneous indication of the phase contents due to non-uniformity and the exponential nature of the photon absorption. Furthermore, without adequate mixing the phases move at different velocities and a single velocity measurement does not give an accurate measure of the flow rates but must be corrected by the use of theoretical models or correlations to account for the relative velocities of the phases. This invention avoids the need for such corrections and their associated uncertainty.

Further, the characteristics of the mixer of the invention are such that the differential pressure across the mixer, when combined with phase fraction information, will provide an accurate measurement of velocity of the flowing fluids over a wide range of flow conditions, including slug flow.

Preferably, the element includes a smoothly contoured surface leading to the part of the element which divides the flowing fluids. Preferably further, the element includes a smoothly contoured surface which leads away from the part of the element which deflects two of the resulting streams so that those streams rotate in opposite senses.

Preferably, the part of the element which divides the flowing fluids into at least two streams within the pipe extends over a significant axial distance which may be about a half to three-quarters of a diameter of the pipe and preferably is about five-eighths of the diameter of the pipe. As the separation of the flows takes place over a significant distance, undue turbulence and disturbance are avoided. Preferably, the part of the element which deflects two of the resulting streams so that those streams rotate in opposite senses extends over a significant axial distance which may be a half to three-quarters of a diameter of the pipe and preferably is about five-eighths of a diameter of the pipe.

Preferably, the surface of the element which faces downstream defines a substantial absence of cavities facing downstream. Preferably, the surface of the element which faces upstream defines a substantial absence of cavities facing upstream.

Preferably further, substantially the entire impingement surface of the element is at an angle of no greater than 85°, preferably 80°, most preferably 70° to the flow direction. Preferably, substantially the entire post impingement surface of the element is at an angle of no greater than 85° to the flow direction, preferably 75°, most preferably 60°. Preferably the maximum angle of direction change of the flow surface of the element is 90°, most preferably 70°.

The most upstream part of the element may comprise a part which presents a rising slope from an inner wall of the pipe to a ridge and may then present a descending slope back to the inner wall of the pipe. The element may comprise a central wall part which divides the pipe into two. The element may comprise a pair of handed curved parts which direct the flow through an angle of 60° to 120°, preferably 80° to 100°, most preferably about 90°.

The element may be made in any suitable fashion and preferably is produced in one or two pieces, for example, by casting or moulding.

According to another aspect of the invention, there is provided apparatus for monitoring flow comprising a mixer according to the first aspect of the invention and means for measuring the pressure drop across the mixer.

By means of the measurement of the pressure drop, flow rate calculations can be carried out.

Preferably, in particular when used for metering mixtures of liquid and gas, the apparatus further includes means for measuring liquid hold-up after the mixer. By measuring the pressure drop and the liquid hold-up, the total velocity of the fluid in the pipe and the liquid flow rate can be calculated.

The means for measuring liquid hold-up may take any suitable form and may comprise phase fraction or liquid fraction measurement instruments. The or each measuring means may comprise at least one radiation source such as an x-ray or preferably gamma radiation source and at least one radiation sensor. The smooth through flow enabled by the mixer of the invention enables consistent and accurate calculations to be carried out of total mixture velocity and mean flow rates. This is particularly important, for example, where oil is produced from one or a group of oil wells. The total homogenised mixture velocity together with phase fraction information can be used to calculate the proportions and quantities of oil, gas and water being produced. Indeed an accuracy of better than 5% can be achieved with this technique over a wide range of flow conditions which represents a considerable improvement over prior techniques.

Preferably the radiation source or sources are arranged to emit radiation at least at two different energies and at least one radiation detector is provided positioned to receive from the source or sources radiation which has passed through the flow, the source or sources emitting radiation at least at two different energies, the or each detector providing a signal to processing means, the processing means being arranged to process the signal to provide a series of chronological values and to group the values by magnitude for analysis by analysis means.

One situation in which fluid flow analysis is important is in the production of oil from an oil well, or group of oil wells. Oil is commonly found mixed with water and gas thus providing a three phase fluid flow. Clearly, it is important to be able to determine how much of the fluid flow is constituted by each of the three phases.

Known apparatus for phase fraction analysis comprises two gamma radiation sources with associated detectors, which are spaced apart along a pipe in the flow direction. The sources emit radiation at different energies. The signals from the detectors are proportional to the gamma radiation received and hence indicate the radiation absorption from the flow. This information enables the phase fractions of the flow to be determined. The phase fractions of the flow may vary widely with time as the flow passes the detectors due the occurrence of slug flow, for example, and the analysis is consequently subject to inaccuracy, particularly as the relationship between radiation absorption and the amount of fluid intercepting the beam is exponential.

According to another aspect of the invention there is provided apparatus for analysing fluid flow in a pipe comprising at least one radiation source to direct radiation through the flow, and at least one radiation detector positioned to receive from the source or sources radiation which has passed through the flow, the source or sources emitting radiation at least at two different energies, the or each detector providing a signal to processing means, the processing means being arranged to process the signal to provide a series of chronological values and to group the values by magnitude for analysis by analysis means.

As the signal becomes a series of values which are grouped, the analysis means can conduct a more sophisticated analysis than simple averaging and a more accurate analysis can be conducted. Preferably, the analysis means is arranged to determine the phase fractions in the flow. Alternatively, or in addition, the analysis means may be arranged to determine the type of flow e.g. slug flow or stratified flow. In addition the analysis of the signals by grouping provides information on the variation of composition of the mixture with time. For example in slug flow the oil/water ratios in the slug and in the thin film between slugs can be individually determined.

Preferably, radiation from the or each source will be measured over a series of short time intervals. In one embodiment, a single detector is provided. In that case, two sources may be provided, each emitting radiation at a different energy. In the prior system, necessary separation of the two sources lead to errors as the radiation beams did not "see" the same section of flow. Because of the processing and analysis which is carried out by the apparatus of the invention, this necessary separation is possible without incurring errors.

As an alternative to two sources, a single source can be used which is arranged to emit radiation of at least two different energies, e.g. a caesium source emitting radiation at 32 keV and 661 keV.

The apparatus is principally intended for use with three phase flow and so preferably radiation at only two different energies is emitted by the source or sources.

The radiation may be X-ray and/or gamma radiation.

The apparatus may include a mixer and means for sensing pressure drop across the mixer. This enables velocity calculations to be carried out when combined with means for sensing liquid hold-up. The sensing means are preferably associated with the analysis means which is arranged to determine flow rate. The means for sensing the liquid hold-up may comprise at least one radiation source to direct radiation through the flow to at least one radiation detector positioned to receive radiation which has passed through the flow from the or each source.

In one embodiment, the apparatus includes only two sources and only two detectors and the analysis means is arranged to determine both phase fraction and flow rate.

Phase fraction is determined using two energies from one of the sources and velocity is determined by comparison of the dynamic radiation signals received by the two detectors spaced axially along the pipe. This arrangement uses the minimum number of components and is thus particularly simple and cost advantageous.

One embodiment of the invention will now be described by way of example and with reference to the accompanying drawings, in which.

Figure 1:
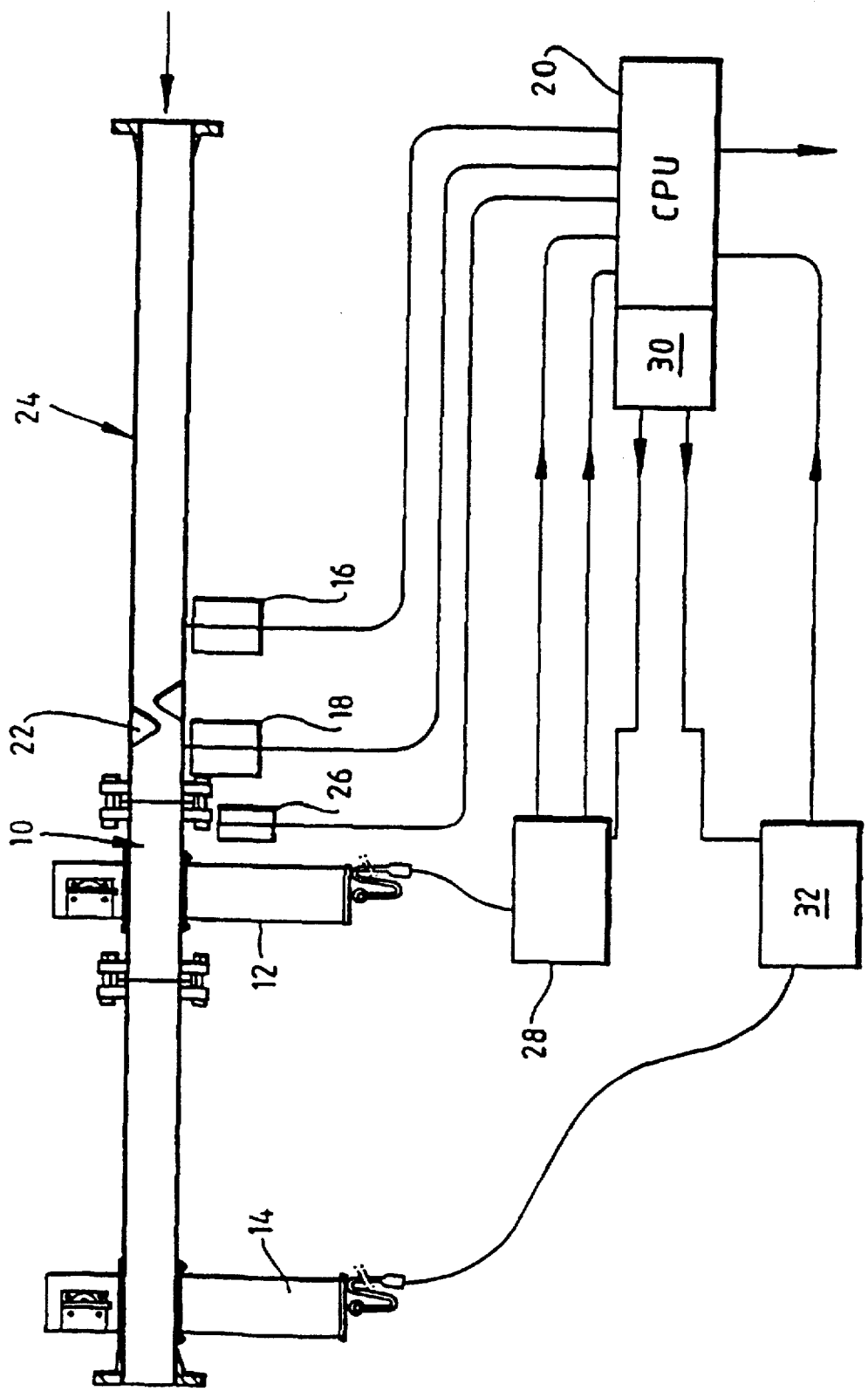
FIG. 1 is a side elevation in partial cross-section of the apparatus of the embodiment.

The apparatus 10 comprises two gamma radiation units 12,14, two pressure transducers 16,18 and a central processing unit 20.

The pressure transducers 16,18 are provided on either side of a static flow mixer 22 within the pipe 24. The pressure transducers 16,18 are connected to the central processing unit 20. Downstream of the mixer 22 is provided a temperature sensor 26 which is also connected to the central processing unit 20. Just downstream of the temperature sensor 26 is provided the first gamma radiation unit 12. The first gamma radiation unit 12 comprises a caesium source of energies 32 keV and 661 keV. The source directs its radiation through the pipe 24 to a single detector to the other side of the pipe 24. The detector is connected to an amplifier and analyzer 28 which has high and low outputs to the central processing unit 20. The amplifier and channel analyzer 28 is powered by a DC power supply 30 adjacent the central processing unit 20. Downstream of the first radiation unit 12 is provided the second radiation unit 14. This includes a single 661 keV caesium source and a thick crystal detector which is connected to a second amplifier and analyzer 32 which is also powered by the power supply 30 and is also connected to the central processing unit 20.

In use, a three phase fluid flow of oil, water and gas flows through the pipe 24 and through the mixer 22. The temperature sensor 26 senses its temperature and the pressure transducers 16,18 upstream and downstream of the mixer 22 provide pressure information to the central processing unit 20 to enable to pressure drop across the mixer 22 to be determined. High and low energy radiation from the source of the first radiation unit 12 is detected by the single detector of the first radiation unit 12 after absorption through the fluid and is processed and analyzed by the central processing unit 20 together with the signals from the second radiation unit 14. The signals from the first radiation unit 12 are chronologically divided and grouped into bands by magnitude for statistical analysis by the central processing unit 20 (which constitutes the aforesaid "processing means" and "analyzing means") to enable an accurate determination of phase fraction to be made. Second radiation unit 14 in combination with the signal from the first radiation unit 12 enables velocity to be calculated and this information together with the calculation of pressure drop enables the total and phase flow rates to be determined. The temperature sensor information is needed to take account of the fact that the gas constitutes a compressible phase.

Alternatively, or in addition, velocity may be derived from pressure drop across the mixer such that the second radiation unit 14 may be omitted.

Figure 2:
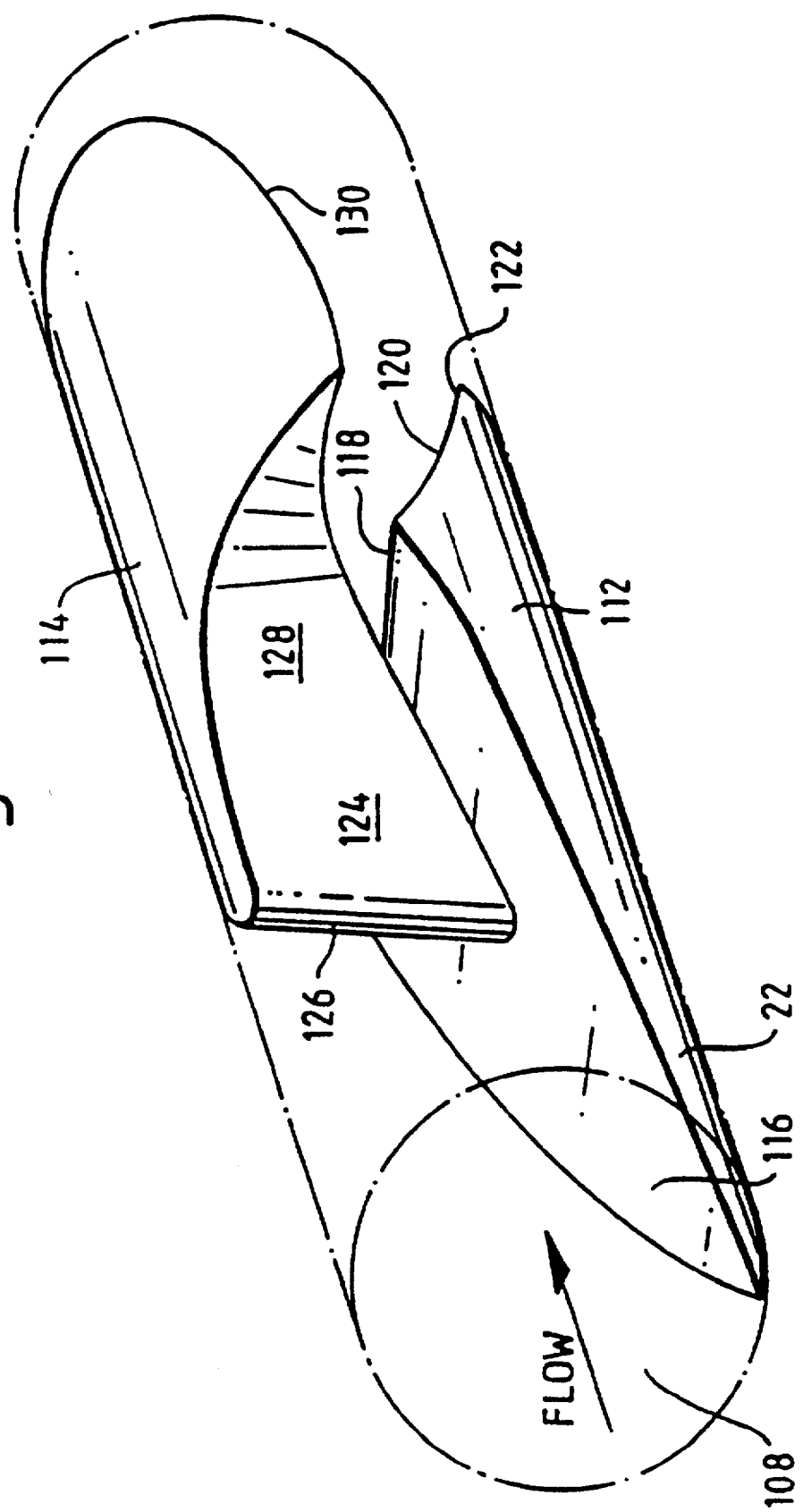
FIG. 2 is a perspective view of the mixer of the embodiment.
Figure 3:
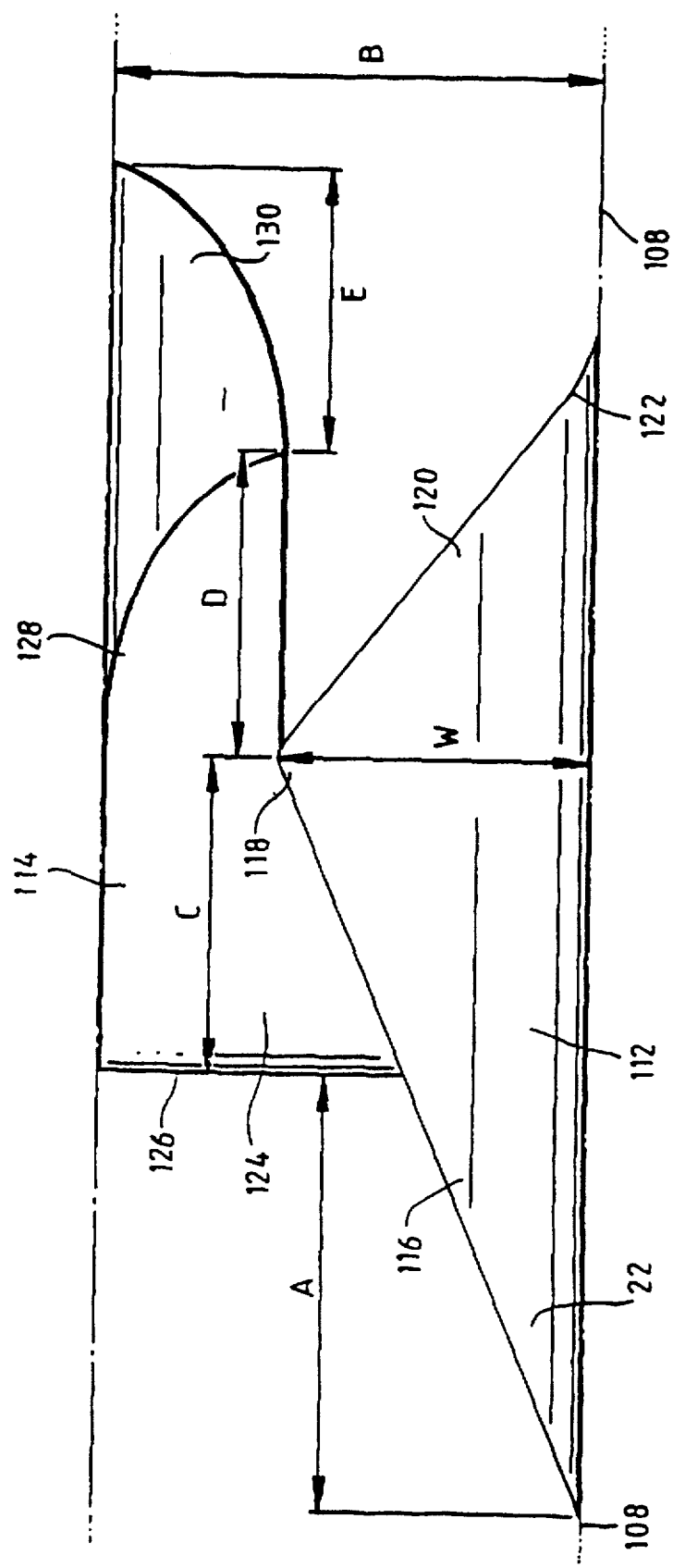
FIG. 3 is a side elevation of the mixer of the embodiment.
Figure 4:
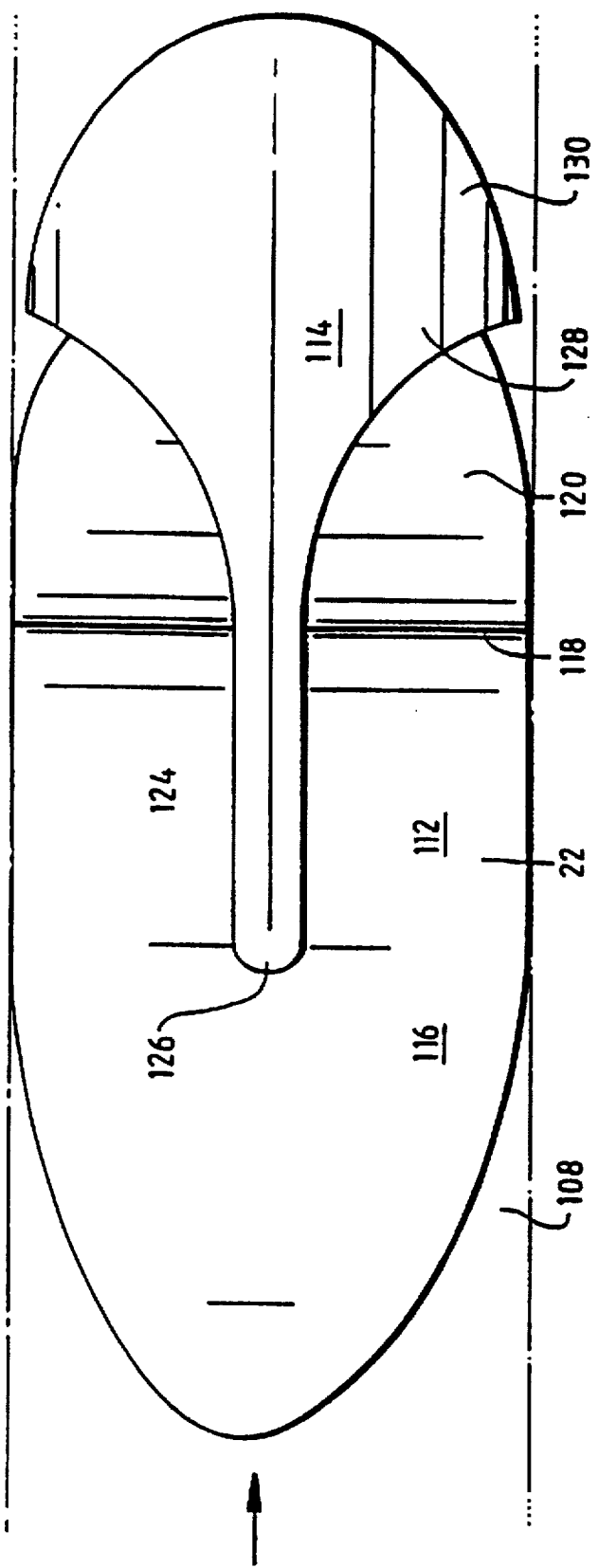
FIG. 4 is a plan view of the mixer of the embodiment.

FIGS. 2 to 4 show the mixer 22 in more detail. The mixer 22 of the embodiment is cast as a single piece, but can be considered to comprise two parts 112,114. The mixer 22 is provided in a cylindrical pipe 108. The first part 112 rises from the floor of the pipe 108 presenting a flat surface 116 to the oncoming flow of fluid through the pipe 108 at an angle of about 20° to the longitudinal axis of the pipe 108. The surface 116 rises to a smoothly curved ridge 118 of height W from which it descends again as a flat surface 120 at an angle of about 40° to the axis of the pipe 108, the angle of descent decreasing close to the floor of the pipe 108 so that the surface 120 smoothly curves to meet the floor of the pipe 108.

The second part 114 is formed to its upstream side as an upright wall 124 of constant thickness and with a rounded front edge 126 against which incoming flow will impinge. The wall 124 intersects the rising surface 116 of the first part 112. Just past the ridge 118, the shape of the second part 114 changes. The lower edge of this central section 128 of the second part 114 continues at the height of the ridge 118, and at the same thickness as the wall 124. The upper part of the central section 128 broadens increasingly in a smoothly curved manner. The degree of broadening of the central section 128 increases along the axis of the pipe until the second part 114 intersects the wall of the pipe 108 at the level of the ridge 118 at which point the angle of the curved surface to the axis of the pipe is about 70°. The downstream section 130 of the second part 114 smoothly curves back towards the wall of the pipe 108 at an increasing angle to the axis of the pipe 10S the greatest angle being about 60° just before intersection with the pipe 108.

In use, flow, for example, of oil, gas and water, passes along the pipe 108 and first impinges upon the ascending surface 116 of the first part which restricts the flow area of the pipe 108. Once the flow reaches the wall 124 it is divided into two and continues to be further restricted until reaching the ridge 118. As the central section 128 of the second part 114 broadens, each flow is subjected to induced rotation, the flows being rotated in different directions. The downstream section 130 of the second part 114 and the descending slope 120 of the first part then slope away from the axis of the pipe 108 and the flow area thus broadens out and the homogenised mixed fluid passes further through the pipe 108. Tt is thus seen that fluid is smoothly guided through the mixer 22.

The distance A from the upstream edge of the surface 116 to intersection with the upstream edge 125 of the wall 124 may be about seven-eighths of the diameter B of the pipe 108. The distance C from the upstream edge 126 of the wall 124 to the ridge 118 may be about five-eighths of the diameter B of the pipe 108. The distance D from the ridge 118 to the end of the central section 128 of the second part 114 may be five-eighths of the diameter B of the pipe 108. The distance E from the end of the central section 128 to the downstream edge of the downstream section 130 of the second part 114, which is further downstream than the downstream edge of the first part 112, may be about nine-sixteenths of the diameter of the pipe. The diameter of the pipe may be about 50–150 mm and in a particular embodiment is 80 mm.

Gamma or X-ray sources and sensors or other means may be provided after the mixer 22 to enable the liquid hold-up to be measured and transducers may be provided to measure pressure drop across the mixer 22 to thereby enable calculation of the total mixture velocity. It has been established experimentally that the pressure drop $D_p$ is linearly related to the product of total and superficial liquid velocities $V_t, V_L$:

$$D_p = a + b\, V_t V_L$$

The liquid hold-up $E_L$ is given by $E_L = V_L/V_t$

Thus: $V_t = [(D_p - a)/(bE_L)]_1$ where a and b are calibration factors dependent mainly upon the properties of the flow components. Because of the nature of the mixer in producing good homogenisation without undue flow disturbance, the factors a and b are relatively insensitive to the ratio of components in particular water, oil and gas. This is unlike the prior static mixers of EP 0395635 for example which produce conditions under which the relevant equations do not hold true with sufficient accuracy. By means of the invention multiphase total velocities and superficial liquid velocities can be measured with an accuracy of better than 5%. The first radiation unit 12 may include two distinct caesium sources, or a single caesium source capable of radiating at both energies. Clearly, other types of radiation source may be used.

In a further embodiment, the first radiation unit 12 and second radiation unit 14 use different energies and source of only a single energy is provided in the first radiation unit.

Clearly the dimensions of the mixer may be varied in different embodiments. The height W of the ridge 118 may be increased to provide a smaller restriction for the flow to pass through, or may be decreased. The length D of the central section 128 which rotates the two streams may be increased to further smooth the flow, or may be decreased. The differential pressure across the mixer can be adjusted in this way to suit the particular installation.

We claim:

1. Apparatus for monitoring multi-phase flow comprising a static mixer for one or more fluids flowing in a pipe, the mixer comprising an element to divide the flowing fluids into at least two separate, streams flowing side by side within the pipe, and to deflect two of the resulting streams so that those streams rotate in opposite senses, the element being shaped so as to maintain movement of the flow in a substantially smooth manner and, means for measuring pressure drop across the mixer and phase fraction measurement instruments.

2. A static mixer as claimed in claim 1, wherein the element includes a smoothly contoured surface leading to the part of the element which divides the flowing fluids.

3. A static mixer as claimed in clam 2, wherein the part of the element which divides the flowing fluids into at least two streams within the pipe extends over a significant axial distance.

4. A static mixer as claimed in claim 1, wherein the element includes a smoothly contoured surface which leads away from the part of the element which deflects two of the resulting streams so that those streams rotate in opposite senses.

5. A static mixer as claimed in claim 4, wherein the part of the element which divides the flowing fluids into at least two streams within the pipe extends over a significant axial distance.

6. A static mixer as claimed in claim 1, wherein the part of the element which divides the flowing fluids into at least two streams within the pipe extends over a significant axial distance.

7. A static mixer as claimed in claim 1, wherein the part of the element which deflects two of the resulting streams so that those streams rotate in opposite senses extends over a significant axial distance.

8. A static mixer as claimed in claim 1, wherein the surface of the element which faces downstream defines a substantial absence of cavities facing downstream.

9. A static mixer as claimed in claim 1, wherein the surface of the element which faces upstream defines a substantial absence of cavities facing upstream.

10. A static mixer as claimed in claim 1, wherein substantially the entire impingement surface of the element is at an angle of no greater than 85°.

11. A static mixer as claimed in claim 1, wherein substantially the entire post impingement surface of the element is at an angle of no greater than 85° to the flow direction.

12. A static mixer as claimed in claim 1, wherein the maximum angle of direction change of the flow surface of the element is 70°.

13. A static mixer as claimed in claim 1, wherein the most upstream part of the element comprises a part which presents a rising slope from an inner wall of the pipe to a ridge and then presents a descending slope back to the inner wall of the pipe.

14. A static mixer as claimed in claim 1, wherein the element comprises a central wall part which divides the pipe into two.

15. A static mixer as claimed in claim 1, wherein the element comprises a pair of handed curved parts which direct the flow through an angle of 60° to 120°.

16. Apparatus as claimed in claim 1, wherein the or each phase fraction measurement instruments comprises at least one radiation source and at least one radiation detector, the radiation source or sources being arranged to emit radiation at least at two different energies and at least one radiation detector being provided positioned to receive from the source or sources radiation which has passed through the flow, the source or sources emitting radiation at least at two different energies, the or each detector providing a signal to a processing means the processing means being arranged to process the signal to provide a series of chronological values and to group the values by magnitude for analysis by analysis means.

* * * * *